US006979991B2

(12) United States Patent
Burns et al.

(10) Patent No.: US 6,979,991 B2
(45) Date of Patent: Dec. 27, 2005

(54) NONDESTRUCTIVE, ELECTRICAL IMPEDANCE-BASED, THERMAL BARRIER COATING INSPECTION

(75) Inventors: Steven M. Burns, West Hartford, CT (US); Sudhangshu Bose, Manchester, CT (US)

(73) Assignee: United Technologies, Corporation, Hartford, CT (US)

( * ) Notice: Subject to any disclaimer, the term of this patent is extended or adjusted under 35 U.S.C. 154(b) by 52 days.

(21) Appl. No.: 10/417,032

(22) Filed: Apr. 16, 2003

(65) Prior Publication Data

US 2004/0207413 A1 Oct. 21, 2004

(51) Int. Cl.$^7$ .............................................. G01N 27/00
(52) U.S. Cl. .................................... 324/71.1; 324/691
(58) Field of Search ................................ 324/662, 663, 324/671, 695, 716, 718, 715, 71.1, 691; 428/678, 630

(56) References Cited

U.S. PATENT DOCUMENTS

| | | | | |
|---|---|---|---|---|
| 3,936,738 A | * | 2/1976 | Maltby | 324/71.1 |
| 4,806,849 A | * | 2/1989 | Kihira et al. | 324/700 |
| 5,015,950 A | * | 5/1991 | Rose et al. | 324/224 |
| 6,054,038 A | | 4/2000 | Davis et al. | |
| 6,072,568 A | | 6/2000 | Paton et al. | |
| 6,099,718 A | | 8/2000 | Duthoo et al. | |
| 6,707,297 B2 | * | 3/2004 | Nath et al. | 324/240 |

FOREIGN PATENT DOCUMENTS

RU    1 675 761 A1    9/1991

OTHER PUBLICATIONS

"In situ of Degradation of a Thermal Barrier Coatings Using Impedance Spectroscopy" by Ogawa et al. Materrials Evaluation,pp 476–481, Mar. 2000.*
S. Vishweswaraiah et al., Non–Destructive Evaluation of Thermal Barrier Coatings by Electrochemical Impedance Spectroscopy, 2003, pp. 1487–1493, published by ASM International, Materials Park, Ohio.
MD Shawkat Ali et al. Evaluation of Degradation of Thermal Barrier Coatings Using Impedance Spectroscopy, Journal of the European Ceramic Society, Jan., 2002, pp. 101–107.
Xin Wang et al., Non–Destructive Evaluation of Thermal Barrier Coatings Using Impedance Spectroscopy, Journal of the European Ceramic Society, Jul., 2001, pp. 855–859.
Kazuhiro Ogawa et al., NDE of Degradation of Thermal Barrier Coating by Means of Impedance Spectroscopy, Apr., 1999, pp. 177–185.
Christensen, R.J., Lipkin, D.M. and Clarke, D.R., Nondestructive Evaluation of the Oxidation Stresses through Thermal Barrier Coatings Using Cr3+ Piezospectroscopy, Appl. Phys. Lett, Dec. 9, 1996, pp. 3754–3756, vol. 69, Issue 24, American Institute of Physics.

* cited by examiner

*Primary Examiner*—N. Le
*Assistant Examiner*—Walter Benson
(74) *Attorney, Agent, or Firm*—Bachman & LaPointe, P.C.

(57) ABSTRACT

A method and apparatus are provided for inspecting a coated substrate such as a multi-layer coating on a substrate of a turbine airfoil. At each of a number of locations along the airfoil a number of frequencies of alternating current are passed through the airfoil. At least one impedance parameter is measured. The measured impedance parameters are utilized to determine a condition of the coating.

20 Claims, 3 Drawing Sheets

NONDESTRUCTIVE, ELECTRICAL IMPEDANCE-BASED, THERMAL BARRIER COATING INSPECTION

BACKGROUND OF THE INVENTION (1) Field of the Invention

This invention relates to inspection of thermal barrier coatings, and more particularly to inspection of coatings on turbine components.

(2) Description of the Related Art

Gas turbine engine components (e.g., blades, vanes, seals, combustor panels, and the like) are commonly formed of nickel- or cobalt-based superalloys. Desired operating temperatures often exceed that possible for the alloys alone. Thermal barrier coatings (TBCs) are in common use on such components to permit use at elevated temperatures. Various coating compositions (e.g., ceramics) and various coating methods (e.g., electron beam physical vapor deposition (EBPVD) and plasma spray deposition) are known.

An exemplary modern coating system is applied to the superalloy substrate by an EB-PVD technique. An exemplary coating system includes a metallic bondcoat layer (e.g., an overlay of NiCoCrAlY alloy or diffusion aluminide) atop the substrate. A thermally insulating ceramic top coat layer (e.g., zirconia stablized with yttria) is deposited atop the bondcoat. During this deposition, a thermally grown oxide layer (TGO), e.g., alumina, forms on the bondcoat and intervenes between the remaining underlying portion of the bondcoat and the top coat.

The coatings are subject to potential defects. For example, the TGO to bondcoat interface tends to suffer from separations/delaminations. Such defects tend to be inherent, so threshold degrees of defect may determine the utility of a given component. Defects may also form during use.

Much of existing inspection involves destructive testing used to approve or reject batches of components. Exemplary destructive testing involves epoxy-mounting and sectioning a component followed by microscopic examination. The TGO is a critical element. This may be viewed via scanning electron microscope (SEM) at 1,000× or higher. Quality standards are used to approve or reject the batch based upon visual interpretation of the SEM images.

Destructive testing suffers from many general drawbacks as do its various particular techniques. The former includes the cost of destroyed components, the inaccuracy inherent in batch sampling, and the cost of time. U.S. Pat. No. 6,352,406 discloses an alternate system involving coating of a pre-couponed turbine blade facsimile in lieu of cutting an actual blade. This may slightly reduce the time spent, but does not address the fundamental problems of destructive testing.

Laser fluorescence has been used for nondestructive evaluation of limited coating parameters. In one example, the beam of a ruby laser is shined on the ceramic top coat and passes therethrough to reach the TGO. The TGO fluoresces and the emitted light passes through the top coat to a sensor. Characteristics of the flurorecence indicate stress in the TGO. Separation/delamination voids are associated with reduced stress and can thus be detected. U.S. Pat. No. 6,072,568 discloses such inspection.

There remains a substantial need for improvement in testing techniques.

BRIEF SUMMARY OF THE INVENTION

Accordingly, one aspect of the invention is a method for inspecting a multi-layer coating on a substrate of a turbine element airfoil. At each of a number of locations along the airfoil, a number of frequencies of alternating current are passed through the airfoil. At least one impedance parameter is measured. Based upon the measured impedance parameters, a condition of the coating is determined.

The current may pass through an electrolyte wetting the airfoil. The method may determine thicknesses of one or more layers of the coating and may identify or characterize voids within the coating or between the substrate and the coating. The method may advantageously be performed in situ with the turbine element installed on a turbomachine. The method may be performed seriatim on a number of turbine elements on the turbonmachine.

Another aspect of the invention is an inspection apparatus. The apparatus may have a source of the current and electrodes for passing the current through the airfoil. The apparatus may have means for measuring the impedance parameter and means for determining the coating condition.

The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

Like reference numbers and designations in the various drawings indicate like elements.

DETAILED DESCRIPTION

Figure 1:
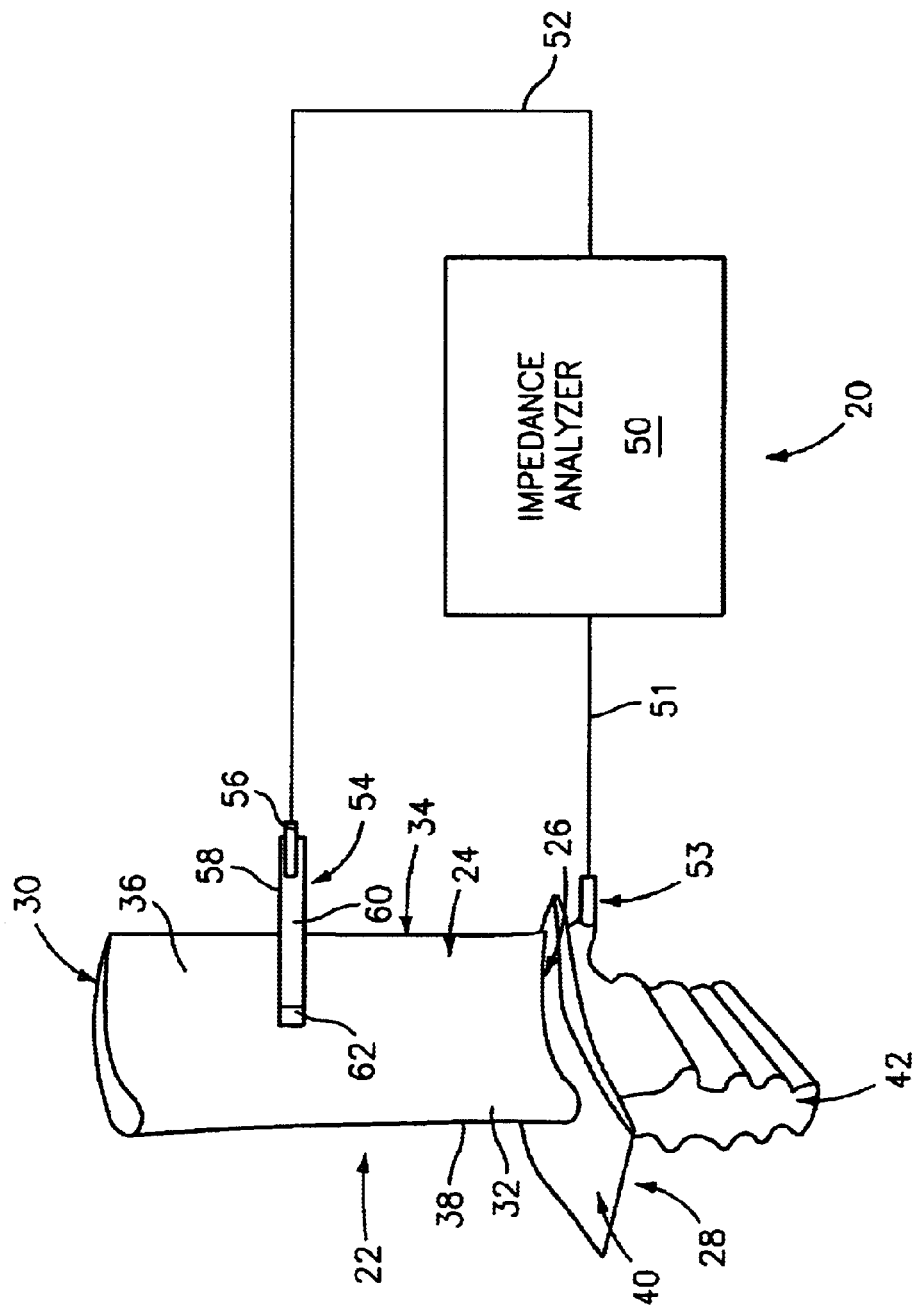
FIG. 1 is a view of a coating test/inspection system.

FIG. 1 shows an apparatus 20 for testing/inspecting a coated item such as a turbine element (e.g., a turbine engine blade 22). The exemplary blade 22 includes an airfoil 24 extending from a root 26 at a platform 28 to a tip 30. The airfoil has leading and trailing edges 32 and 34 separating pressure and suction sides 36 and 38. The platform has an outboard portion 40 for forming an inboard boundary/wall of a core flowpath through the turbine engine. A mounting portion or blade root 42 depends centrally from the underside of the platform 40 for fixing the blade in a disk of the turbine engine. In an exemplary embodiment, the portion 40 and airfoil 24 are coated.

The exemplary system 20 includes an impedance analyzer 50 coupled by conductors 51 and 52 to a pair of electrodes 53 and 54. The first electrode 53 may be a standard reference electrode contacted with an uncoated portion of the platform. The second electrode 54 is contacted with a coated portion of the blade and, therefore, is advantageously provided as a wetting electrode. The wetting electrode 54 includes a standard reference electrode 56 mounted in a proximal end of a tubular vessel 58 and contacting an electrolyte 60 within the vessel. A check valve 62 is mounted in a distal end of the vessel 58. When the check valve 62 is contacted with the coating, it establishes fluid communication between the contact site and the interior of the vessel providing a small wetting of the coated surface with the electrolyte and providing an electrical path through the electrolyte from the coating to the reference electrode 56.

Figure 2:
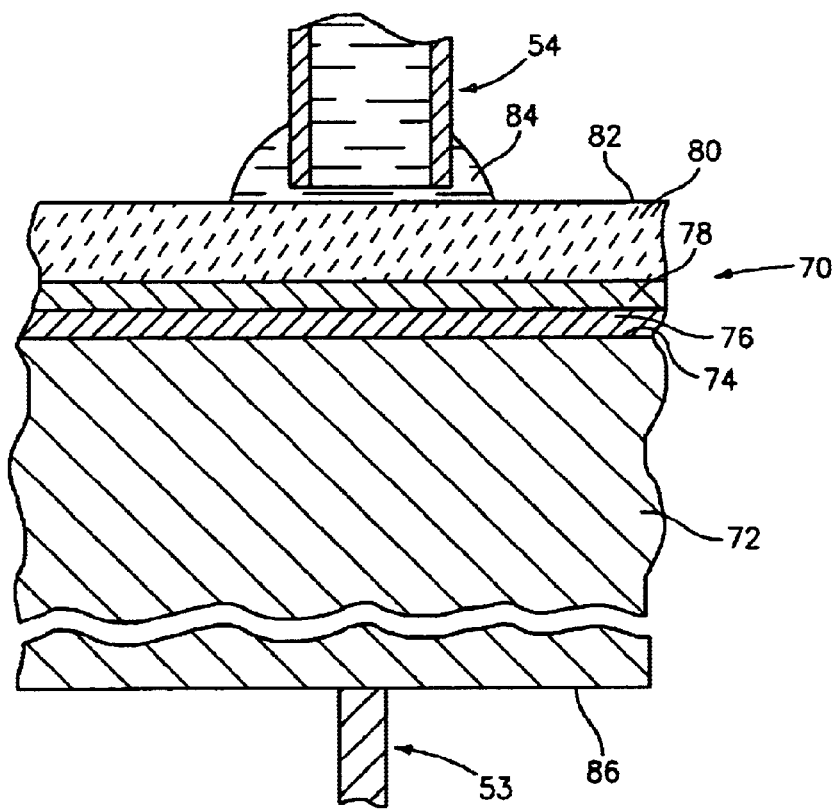
FIG. 2 is a sectional view of a coated item.

FIG. 2 shows further details of the coating 70 on a metallic substrate 72 of the blade. The blade has an outer surface 74 atop which the coating layers are deposited. The layers include a metallic bondcoat 76 atop the substrate surface 74, an in situ formed TGO layer 78 atop the bondcoat, and a ceramic topcoat 80 atop the TGO and having an external surface 82. Contact is made between the electrode 54 and the surface 82 via the wetting electrolyte 84. Direct electrical contact is made between the electrode 53 and an exposed uncoated surface 86 of the substrate.

Figure 3:
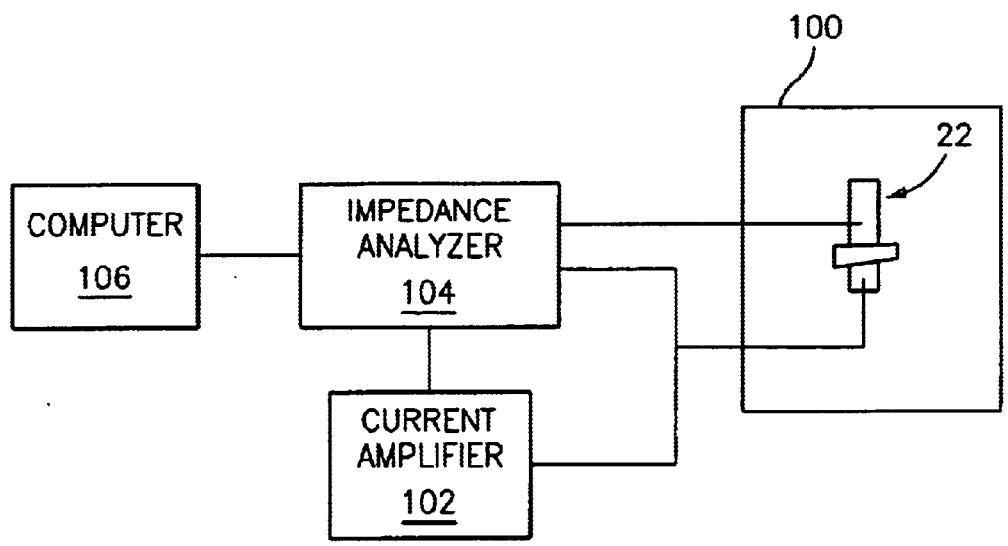
FIG. 3 is an alternate view of a test/inspection system.

In a laboratory setting, the system 20 of FIG. 1. may include an environmental control chamber 100 (FIG. 3) for containing the blade 22 during testing and that controls various properties of temperature, humidity, pressure, and the like. The current is provided by a current amplifier 102 coupled to an impedance analyzer 104 for measuring impedance parameters. The impedance analyzer 104 is coupled to analysis equipment such as a computer 106. The computer may display results of the measured parameters and perform analyses to determine quantitative and qualitative properties of the coating based on the received parameters.

Figure 4:
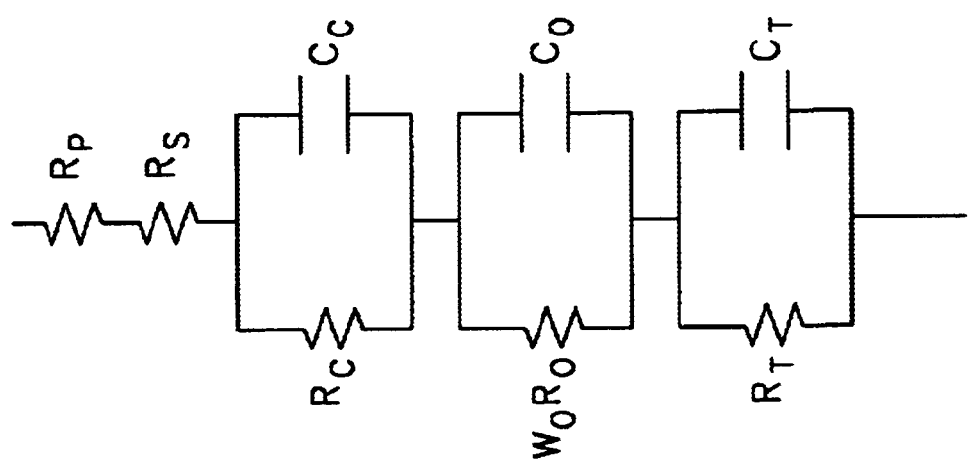
FIG. 4 is a circuit equivalent model of a coating.

Various theoretical, empirical or hybrid models may be used to determine coating properties. Such properties may include the layer thicknesses and the presence, size, and quantity of imperfections (e.g., voids within layers or between layers (e.g., separations and delaminations)). FIG. 4 shows a basic electric circuit model. From one end of the circuit to the other, the resistance of the electrode 54 (FIG. 1) is shown as $R_P$ in series with an electrolyte solution resistance $R_S$. This, in turn, is in series with the parallel combination of a topcoat resistance $R_C$ and a topcoat capacitance $C_C$. This, in turn, is in series with the parallel combination of a TGO resistance $R_O$ multiplied by a Warburg coefficient $W_O$ and a TGO capacitance $C_O$. This is, in turn, in series with the parallel combination of a resistance $R_T$ of the interface between the superalloy and bondcoat and an interface capacitance $C_T$.

Figure 5:
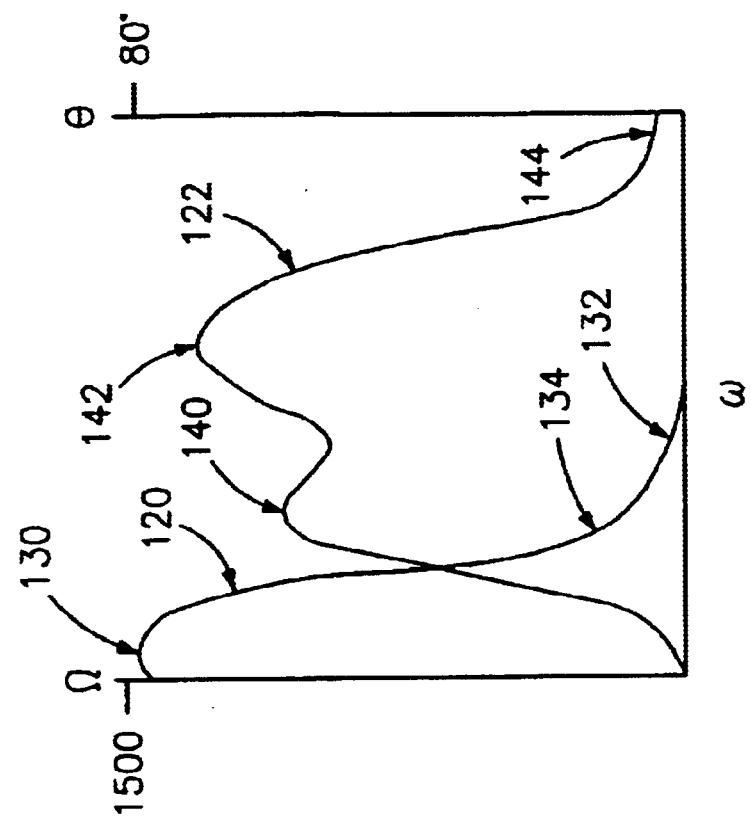
FIG. 5 is a graph of impedance and phase angle against frequency for an exemplary coating.

FIG. 5 shows an exemplary graph 120 of impedance Ω against frequency ω. An exemplary impedance scale is 0–1500 Kohm/cm². FIG. 5 further shows an exemplary graph 122 of phase angle θ against frequency. An exemplary phase angle scale is 0 to 80°. In this model, roughly the location of the impedance peak 130 is indicative of $R_T$. The location of the impedance tail 132 is indicative of $R_P$. In the location of the transition 134 is indicative of $R_C$ and $R_o$. The location of a low frequency phase angle peak 140 is indicative of $C_o$ and the location of a high frequency phase angle peak 142 is indicative of $C_C$. The location of a tail 144 is indicative of $C_T$. The wetting electrode may be moved seriatim to a plurality of positions on the blade and impedance measurements taken. Analysis of data from such multiple positions may be used to even better determine coating properties.

Less environmentally controlled tests may be performed in situ on an assembled engine such as performing periodic tests on an aircraft engine. Such testing may be used to determine wear and other degradation parameters and determine remaining life of the turbine element. Alternative tests may involve contacting two probes with the coating. This may be appropriate where convenient access to uncoated portions is difficult. Relatively complex models could be used for such a situation.

One or more embodiments of the present invention have been described. Nevertheless, it will be understood that various modifications may be made without departing from the spirit and scope of the invention. For example, details of the particular turbine elements, coatings, test conditions, and examination criteria may influence the structure of the inspection apparatus and implementation of the inspection methods. Accordingly, other embodiments are within the scope of the following claims.

What is claimed is:

1. A method for inspecting a muli-layer coating on a substrate of a turbine element airfoil comprising:
   for each of a plurality of locations along the airfoil:
      for each of a plurality of frequencies of alternating current:
         passing said current through the airfoil; and
         measuring at least one impedance parameter; and
      determining a condition of the coating;
   wherein said current is passed between first and second electrodes, and
   wherein an ionically conductive liquid is applied at contact points of the first and second electrodes with the coating.

2. The method of claim 1 wherein said determining comprises determining a thickness of at least one layer of the coating.

3. The method of claim 1 wherein said determining comprises identifying a void within the coating or between the substrate and the coating.

4. The method of claim 1 performed while the turbine element is installed on a turbomachine.

5. The method of claim 4 performed seriatim on a plurality of turbine elements on said turbomachine.

6. The method of claim 1 performed while the turbine element is installed on a gas turbine engine.

7. The method of claim 1 wherein for each said location the current is passed between a first electrode uniquely positioned relative to said location and a second electrode commonly positioned.

8. The method of claim 1 wherein for each said location the current is passed between a first electrode uniquely positioned relative to said location and a second electrode uniquely positioned.

9. The method of claim 1 further comprising:
   approving or rejecting the turbine element.

10. The method of claim 1 further comprising:
   determining a remaining useful life of the turbine element.

11. A method for inspecting a coated item comprising:
   electrically coupling first and second electrodes of a test apparatus to the item;
   passing an alternating current between the electrodes, the current passing through at least:
      a ceramic layer;
      a metallic substrate;
      a bondcoat layer between the ceramic layer and the metallic substrate; and
      an additional layer between the bondcoat layer and the ceramic layer; and
      measuring an impedance parameter.
   wherein said electrically coupling comprises applying ionically conductive liquid at contact location between-the first and second electrodes and thecoated item.

12. The method of claim 11 wherein said liquid is applied prior to contacting the item with the electrodes.

13. The method of claim 11 further comprising:
   responsive to said impedance parameter, approving or rejecting the item.

14. A method for inspecting a coated item, the item comprising:
   a ceramic layer;

a metallic substrate;

a bondcoat layer between the ceramic layer and the metallic substrate; and an additional layer between the bondcoat layer and the ceramic layer, the method comprising:

a step for electrically coupling a test apparatus to the item via two electrode, each using an ionically conductive liquid; and a step for obtaining an impedance spectrum characteristic for a location on the item.

15. The method of claim 14 wherein the method further comprises a step for identifying a physical characteristic of the item related to the impedance spectrum characteristic.

16. The method of claim 15 wherein said physical characteristic comprises a thickness of at least one of the bondcoat layer, the additional layer, and the ceramic layer.

17. The method of claim 15 wherein said physical characteristic comprises a size characteristic of a void.

18. The method of claim 15 wherein said physical characteristic comprises a size characteristic of a void between an adjacent two of the substrate, the bondcoat layer, the additional layer, and the ceramic layer.

19. A method for inspecting a coated item, the item comprising:

a ceramic layer;

a metallic substrate;

a bondcoat layer between the ceramic layer and the metallic substrate; and an additional layer between the bondcoat layer and the ceramic layer, the method comprising:

a step for electrically coupling a test apparatus to the item; and a step for obtaining an impedance spectrum characteristic for a location on the item; and a step for identifying a physical characteristic of the item related to the impedance spectrum characteristic, said physical characteristic comprising a size characteristic of a void between an adjacent two of the substrate, the bondcoat layer, the additional layer and; the ceramic layer.

20. A method for inspecting a multi-layer coating on a substrate of a turbine element airfoil comprising:

for each of a plurality of locations along the airfoil:

for each of a plurality of frequencies of alternating current:

passing said current through the airfoil; and measuring at least one impedance parameter; and determining a condition of the coating, including identifying a physical characteristic of the airfoil related to the impedance parameter, said physical characteristic comprising a size characteristic of a void between an adjacent two of the substrate, a ceramic layer, a bondcoat layer between the substrate and the ceramic layer, and an additional layer between the bondcoat layer and the ceramic layer.

* * * * *

UNITED STATES PATENT AND TRADEMARK OFFICE
CERTIFICATE OF CORRECTION

PATENT NO. : 6,979,991 B2 Page 1 of 1
APPLICATION NO. : 10/417032
DATED : December 27, 2005
INVENTOR(S) : Steven M. Burns et al.

It is certified that error appears in the above-identified patent and that said Letters Patent is hereby corrected as shown below:

In column 4, claim 11, line 58, "thecoated" should read --the coated--.

In column 5, claim 14, line 7, "electrode" should read --electrodes--.

In column 6, claim 19, line 11, "layer and;" should read --layer, and--.

Signed and Sealed this

Nineteenth Day of December, 2006

JON W. DUDAS
*Director of the United States Patent and Trademark Office*